United States Patent [19]

Craythorne et al.

[11] Patent Number: 4,865,023

[45] Date of Patent: Sep. 12, 1989

[54] ANKLE SUPPORT APPARATUS

[76] Inventors: Colin M. Craythorne; George Parsley; Robert W. Lowe, all of 2828 First Avenue, Huntington, W. Va. 25701

[21] Appl. No.: 183,938

[22] Filed: Apr. 20, 1988

[51] Int. Cl.⁴ ............................................. A61H 5/00
[52] U.S. Cl. .................................. 128/80 H; 128/166
[58] Field of Search ..................... 128/80 E, 80 H, 166

[56] References Cited

U.S. PATENT DOCUMENTS

| 1,129,525 | 2/1915 | Severy | |
|---|---|---|---|
| 1,397,095 | 11/1921 | Hamilton | |
| 2,847,991 | 8/1950 | Andrews | 128/80 E |
| 2,994,322 | 8/1961 | Cullen et al. | 128/80 H |
| 3,506,000 | 4/1970 | Baker | 128/166 |
| 3,699,959 | 10/1972 | Garrahan et al. | 128/166 |
| 3,834,377 | 9/1974 | Lebold | 128/80 H |
| 3,986,501 | 10/1976 | Schad | 128/80 E |
| 4,133,311 | 1/1979 | Karczewski | 128/80 H |
| 4,289,122 | 9/1981 | Mason et al. | 128/80 E |
| 4,323,058 | 4/1982 | Detty | 128/80 H |
| 4,392,487 | 7/1983 | Selner et al. | 128/80 H |
| 4,440,158 | 4/1984 | Shapiro | 128/80 H |
| 4,495,942 | 1/1985 | Palumbo | 128/80 H |
| 4,517,968 | 5/1985 | Greene et al. | 128/80 H |
| 4,523,394 | 6/1985 | Lindh et al. | 36/89 |
| 4,527,556 | 7/1985 | Nelson | 128/80 H |
| 4,547,981 | 10/1985 | Thais et al. | 36/89 |
| 4,556,054 | 12/1985 | Paulseth | 128/80 H |
| 4,590,932 | 5/1986 | Wilkerson | 128/80 H |
| 4,621,648 | 11/1986 | Ivany | 128/166 |
| 4,638,799 | 1/1987 | Grisor | 128/80 H |
| 4,646,726 | 3/1987 | Westin et al. | 128/80 H |
| 4,651,726 | 3/1987 | Holland | 128/166 |
| 4,753,229 | 6/1988 | Sutherland | 128/166 |

FOREIGN PATENT DOCUMENTS

| 183418 | 4/1907 | Fed. Rep. of Germany | 128/166 |
|---|---|---|---|
| 511968 | 11/1930 | Fed. Rep. of Germany | 128/80 H |
| 817195 | 8/1929 | United Kingdom | 128/80 H |
| 0001659 | 5/1982 | World Int. Prop. O. | 128/80 H |

OTHER PUBLICATIONS

M-F Athletic Company, Inc.—letter.
Alimed, Inc.—CAMO Ankle Support advertisement.
Orthopedic Technology, Inc.—Orthotech Walker advertisement.
Aircast, Inc.—Air-Stirrup Ankle Brace advertisement.
3D Orthopedic, Inc.—3D Funtional Ankle Brace advertisement.
Jung Corporation—FUTURO Ankle Brace advertisement.
McDavid—A-101 Ankle Guard advertisement.

Primary Examiner—Edgar S. Burr
Assistant Examiner—Tanya Lamb
Attorney, Agent, or Firm—Lahive & Cockfield

[57] ABSTRACT

This invention relates to an ankle support device which may be worn separately or incorporated into footwear, and which provides a method for bracing the ankle against lateral sprains. The ankle support device has a bracing pad which seats on the lateral side of the foot on the anterior portion of the heel bone and braces against the underside of the lateral malleolus. The bracing pad is secured to the foot by means of a stirrup strap which attaches at the upper end to an ankle cuff and at the lower end to a heel cup. The pad is anatomically configured to support the lateral side of the heel bone and the inferior side of the lateral malleolus, thereby resisting inversion, preventing injury, and providing support during the healing process.

25 Claims, 8 Drawing Sheets

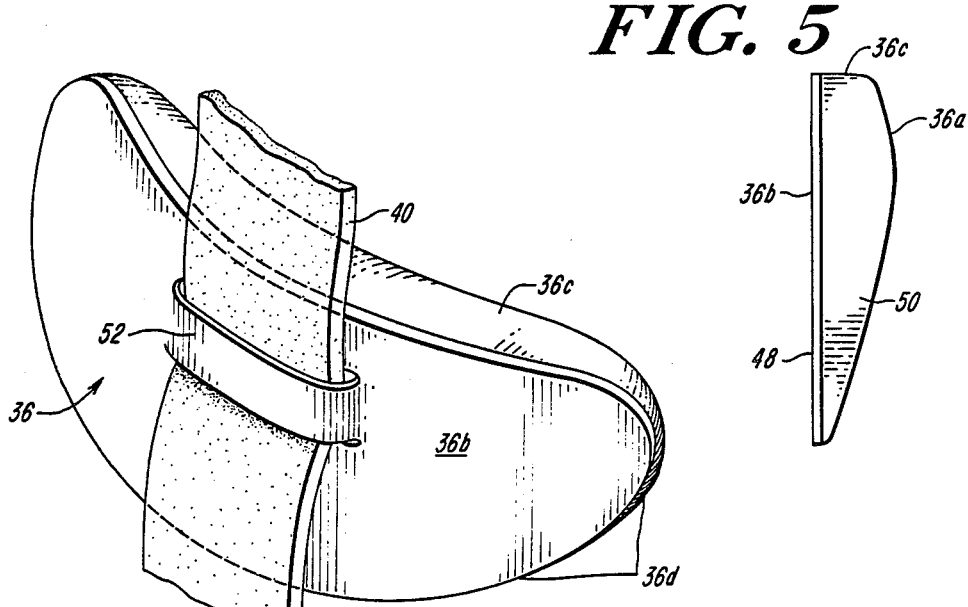
FIG. 5
FIG. 4
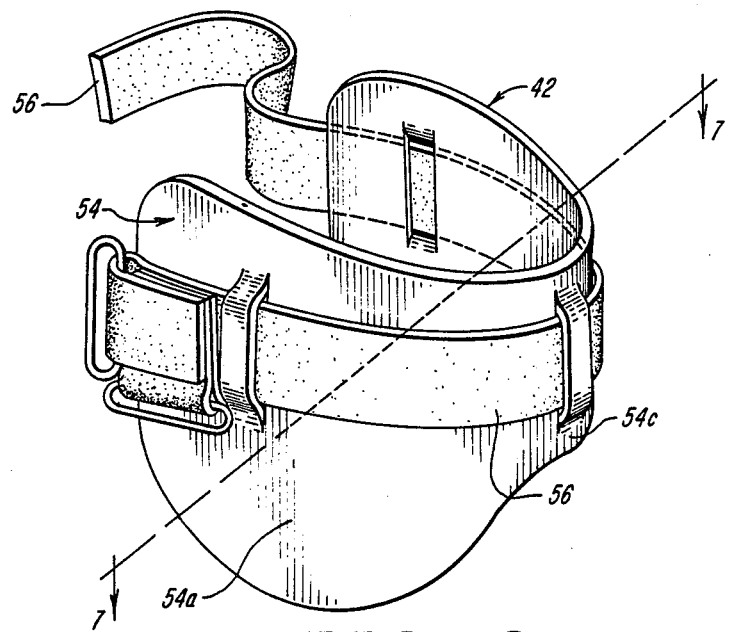
FIG. 6

ANKLE SUPPORT APPARATUS

BACKGROUND

This invention relates to ankle support apparatus and to footwear incorporating ankle support structures. In particular, it provides ankle support apparatus for use in protecting against injury and for use during recovery from an ankle injury. The support apparatus is particularly useful with regard to sprains of the lateral ligaments of the ankle. This type of injury commonly occurs from undue inversion of the ankle.

The invention provides ankle support apparatus that can be a separate device, e.g. for wearing without conventional footwear and, alternatively, inside footwear, and that can be incorporated in footwear.

Sprains of the lateral ankle ligaments are a common injury to humans. Protection from such injuries have included taping and bracing. Surgical operations are available to repair sprained ligaments directly, and other operations are available to reconstruct sprains. Many surgical operations endeavor to enhance the ligament strength in the ankle on the outer, lateral side. Such operations can provide a stable ankle, good performance for sports, and low discomfort. However, they often significantly reduce passive inversion of the ankle.

The prior art regarding devices for bracing the ankle against lateral sprains is relatively extensive, and includes the following U.S. Pat. Nos. 1,129,525 of Severy; 1,397,095 of Hamilton; 4,323,058 of Detty; 4,440,158 of Shapiro; 4,523,394 of Lindh et al; 4,527,556 of Nelson; 4,547,981 of Thais et al; 4,556,054 of Paulseth; and 4,651,726 of Holland An object of this invention is to provide readily removable and replaceable ankle support apparatus that provides secure bracing against lateral inversion. Another object is to provide such ankle support apparatus that provides reliable inversion support.

Further objects of the invention include the provision of ankle support apparatus of the above character that is convenient to use, light in weight, has small bulk, and is hence unobtrusive and which is convenient and comfortable for the wearer. It is also an object that the support apparatus be suitable for low cost manufacture.

Another object is to provide ankle support apparatus of the above character that is suited for use separate from footwear and that, alternatively, can be incorporated into footwear.

Other objects of the invention will in part be obvious and will in part appear hereinafter.

GENERAL DESCRIPTION

An ankle support device according to the invention has a bracing pad that seats on the lateral side against the heel bone or os calcis. The bracing pad also seats against the underside of the lateral malleolus. The bracing pad is configured anatomically to supportingly engage both laterally against the os calcis and upwardly against the lateral malleolus. The support device carries the bracing pad to bear laterally against the os calcis and to bear upward on the lateral malleolus when the ankle inverts, in a manner that resists undue inversion and thereby prevents injury and provides support during healing.

According to one practice of the invention, the structure of the support device which carries and deploys the bracing pad includes a vertically extending lateral stirrup strap, on which the bracing pad is carried. The stirrup strap is secured at an upper end to an ankle encircling strap or ankle wrap. The ankle wrap preferably has a cuff that encircles the ankle seated on the lateral malleolus, and preferably on both the malleoli, and resists downward movement on the ankle even when the strap is tensioned.

A further preferred practice of the invention employs an ankle wrap having a cuff that is flared, with a smaller top circumference, in conformance with the upper conical flare of the upper portions of the malleoli. Additional features of the ankle cuff according to the invention are an asymmetrical cross section in a horizontal plane, with a long and hence major front-to-back, i.e. longitudinal, axis and a lesser, i.e. minor, side-to-side or transverse axis. The cuff, which has significant stiffness, has relatively short height at the back, providing some relief of pressure at the Achilles tendon, and considerably greater height on both side, to overlap the malleoli. These structural features, combined with a circumference-adjusting strap, enable the ankle cuff to seat yet comfortably above the ankle joint and to resist sliding downward, which would undesirably slacken either or both elevator straps. Further, the structural features of the ankle cuff hold it reliably in place rotation-wise, i.e. it resists twisting on the ankle. Instead the cuff enables the wrap to provide secure reliable anchorage for the upper end of the elevator strap system.

One practice of the invention further provides a heel cup to which the lower end of the stirrup strap is attached. The heel cup extends under the heel of the wearer towards the metatarsal base and preferably wraps around the sides and back of the heel with a structure which moves with heel, e.g. that resists slippage relative to the heel, when the heel inverts.

A medial stirrup strap extending between the ankle wrap and a heel cup is a preferred optional practice for enhancing support and stability of the support device. The medial strap preferably has negligible slack during normal ankle posture and hence tensions under eversion.

One preferred anatomical configuration of the bracing pad employs a broad, spade-like wedging contour. This feature of the invention endows the bracing pad with relatively small height and considerably greater lateral length. A two-to-one aspect ratio of length to height is typical for one preferred practice. The lower contour of the pad in this embodiment is concavely rounded and the upper contour is substantially flat or slightly convex to receive and accommodate the lower rim of the lateral malleolus. The size of the pad preferably conforms generally to the lateral surface of the os calcis, to enhance seating below the lower rim of the lateral malleolus.

The thickness of the bracing pad preferably also is contoured. One embodiment has a substantially uniform maximal thickness along an upper third portion combined with diminishing thickness, and hence an outward taper, to the lower peripheral rim.

According to further features of the invention, an article of footwear carries a bracing pad on the lateral side bearing against the os calcis and the underside of the lateral malleolus. The footwear article can include a lateral stirrup strap for carrying the bracing pad at an adjustable elevation for maximal support and comfort. An ankle encircling adjustable strap on the footwear, above the malleoli, can anchor the upper end of this stirrup strap element for secure and reliable deployment of the bracing pad.

The footwear can employ a bracing pad deployed on a stirrup strap element or other structure in this manner either internal of the normal footwear shell or externally.

The further structure of the footwear article which supports and encloses the heel of the wearer can provide anchorage for the lower end of the stirrup strap element, e.g. can serve as the heel cup as described above.

These and further features of ankle support devices according to the invention as described and illustrated herein provide a high level of ankle support, particularly against undue lateral inversion. The support devices can also provide support against undue eversion. Ankle support structures according to the invention provide a high degree of user comfort and convenience, in addition to both protection against injury and support bracing during recovery from lateral strain and other ankle injuries.

BRIEF DESCRIPTION OF THE DRAWINGS

The invention accordingly comprises the features of construction, combinations of elements and arrangements of parts exemplified in the constructions hereinafter set forth and in the article described, and the scope of the invention is indicated in the claims. For a fuller understanding of the nature and objects of the invention, reference is to made to the following detailed description and the accompanying drawings in which:

FIGS. 4 and 5 are detail views of the bracing pad of the support device of FIG. 3;

FIGS. 6 and 7 further illustrate the ankle wrap and cuff of the support device of FIG. 3;

DESCRIPTION OF ILLUSTRATED EMBODIMENTS

Figure 1:
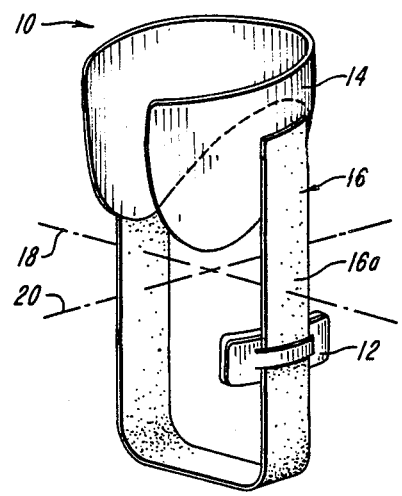
FIG. 1 is a diagrammatic perspective view of an ankle support device according to the invention.

An ankle support device 10 according to the invention has, as FIG. 1 shows for a left ankle, a bracing pad 12 that seats on the lateral side of a wearer, against the heel bone or os calcis and against the underside of the lateral malleolus. An ankle cuff 14 of the device encircles the leg of the wearer seated on the upper side of the lateral and medial malleoli.

A stirrup element 16 connects at the top upper ends of lateral and medial branches 16a and 16b respectively of its U-shaped configuration to the lateral and medial sides of the ankle cuff 14. The span of the stirrup element between the branches passes under the wearer's heel at a location substantially below the malleoli. The stirrup branches thus extends substantially vertically, in normal disposition, along the lateral and medial sides of the wearer's ankle. The stirrup element 16 carries the bracing pad 12 on the lateral branch 16a.

The stirrup branches resist tensile elongation and can otherwise be flexible and compliant.

The ankle cuff 14 is conically flared and otherwise contoured to seat substantially fixedly on the upper sides of the malleoli. It resists movement vertically, i.e. up and down on the wearer, and resists rotation, i.e. twisting about the ankle of the wearer.

The ankle support device 10 imposes minimal impediment or restriction to normal flexure of a wearer's ankle about a horizontal side-to-side, i.e. transverse, axis 18. This is the motion normally involved in walking, and includes extending the foot to point the toes and retracting the foot to raise the toes. During this walking-type flexure, the elements of the support device 10 remain essentially in place on the wearer and the stirrup branches flex to accommodate the wearer's movement.

The ankle support device 10 however resists lateral inversion of the wearer's ankle. This is flexure of the foot about a normally horizontal front-to-back, i.e. longitudinal, axis 20. Both axes 18 and 20 interact the ankle joint, at the malleoli, as shown. In particular, the tensile strength of the lateral stirrup branch 16a resists lateral inversion. The tensile strength resistance of this stirrup branch, which becomes increasingly taut with increasingly lateral inversion, thus acts similar to lateral ligaments of the wearer's ankle and thereby reinforces and aids the lateral ligaments in resisting the lateral inversion motion.

The ankle support device 10 additionally resists lateral inversion by the action of the bracing pad 12 laterally inward against the os calcis and upward against the lateral malleolus. These bracing forces result from lateral inward and upward urging which the tensioned stirrup lateral branch 16a imparts to the bracing pad which the branch carries.

Figure 2:
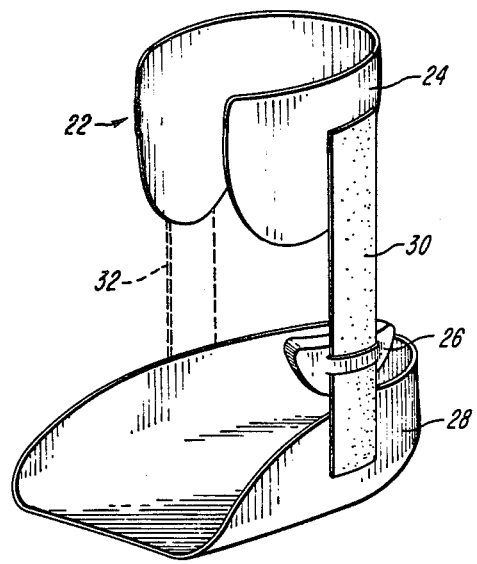
FIG. 2 is a similar view of another ankle support device according to the invention.

FIG. 2 shows an ankle support device 22 according to the invention and generally similar to the device 10 of FIG. 1 with an ankle cuff 24 and a lateral bracing pad 26. A heel cup 28 of the device seats under the heel of the wearer and has sides that partially encircle the sides and back of the heel to move with the heel of the wearer. A lateral stirrup strap 30 is connected at its upper end to the ankle cuff 24 and at a lower end to the heel cup 28. The strap carries the bracing pad 26 disposed along lateral side the os calcis of the wearer and the underside of the lateral malleolus.

The ankle support device 22 of FIG. 2 operates similar to the device 10 of FIG. 1, in that upon lateral inversion of the wearer's ankle, the lateral strap 30 becomes increasingly taut. This tension of the strap, secured between the substantially fixed ankle cuff 24 and the heel cup 28 that moves closely with the heel of the wearer, resists the lateral inversion motion. The tensioned lateral strap also increasingly urges the bracing pad 26 laterally against the os calcis and upwardly against the lateral malleolus to enhance the resistance to lateral inversion.

FIG. 2 indicates with dashed lines that the ankle support brace 22 can employ, as an optional element, a medial stirrup strap 32, where desired for added stability and to support against medial inversion of the wearer's ankle.

Figure 3:
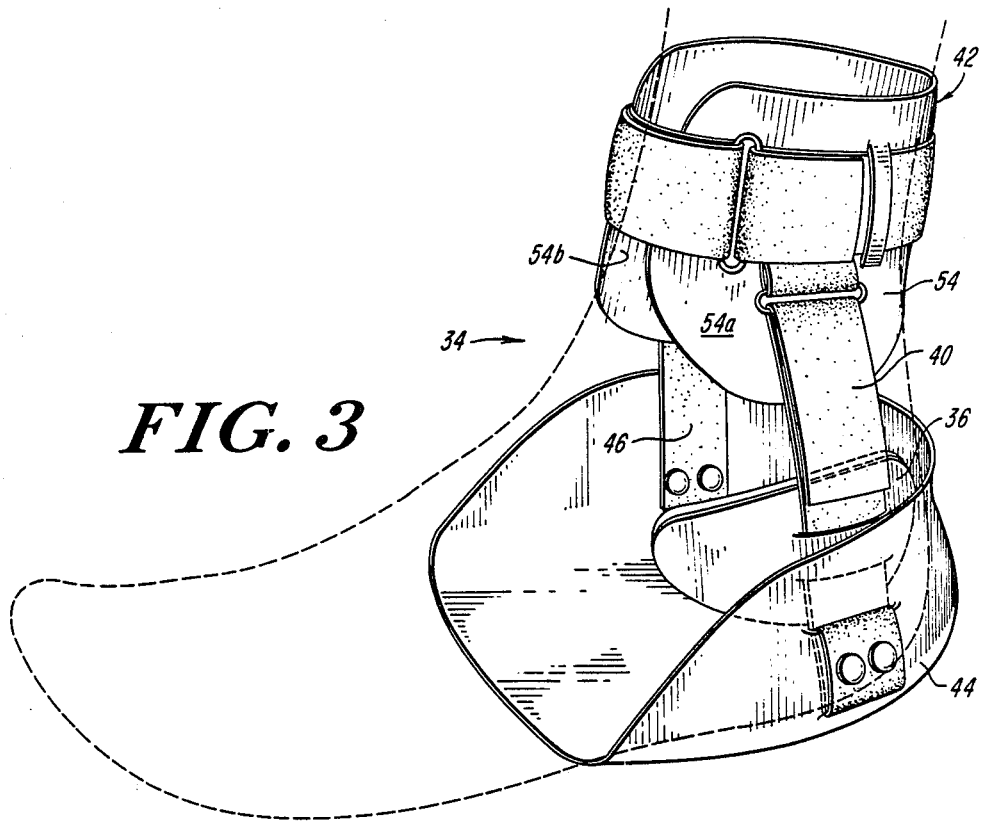
FIG. 3 shows one preferred embodiment of an ankle support according to the invention fitted onto a wearer.

An ankle support device 34 shown in FIG. 3, and in detailed views of FIGS. 4–8, employs a bracing pad 36 carried on a lateral strap 40 that spans between an ankle wrap 42 and a heel cup 44. The illustrated support device 34 includes an optional medial strap 46 that spans between the medial sides of the cuff 42 and the cup 44, substantially parallel to the lateral strap 40.

The bracing pad shown in 36 FIGS. 4 and 5, has an inner bearing surface 36a contoured to the anatomically rounded recess located on the lateral side of a foot at the anterior portion of the heel bone and inferior to the prominence of the malleolus or ankle bone. The pad 36 is substantially non-yielding, i.e., is substantially rigid or stiffly resilient and has a relatively large bearing surface, typically for contacting the wearer along a distance greater than the front-to-back, lateral span of the lateral malleolus. The peripheral contour of the illustrated bearing surface 36a has an upper rim 36c that is slightly concave to receive and fit around the rounded malleolus, and has a side and lower rim 36d that is substantially continuously convexly rounded. This overall contour is roughly similar to that of a short, broad tool blade, as on a shovel. The bracing pad backwall 36b is straight as viewed in cross section in a vertical plane, as in FIG. 5, and is curved as viewed in cross section in a horizontal plane. The inner bearing surface 36a is similarly curved in a horizontal plane and is horizontally concave as viewed in a vertical plane, with substantial thickness in an upper portion and diminished thickness below. The bracing pad hence has a plano-concave wedge-like cross-section, as appears in FIG. 5.

One typical construction for the illustrated bracing pad 36 employs a stiff panel 48 of synthetic polymer that forms the back wall 36b and which carries a firm cushion material such as a closed cell synthetic foam 50 that forms the inner wall 36a. A strap-engaging loop 52 on the panel 48 projects outwardly from the backwall 36b for slideably receiving, with selectively adjustably interference, the lateral strap 40, as appears in FIG. 4. One embodiment of the pad 36 is made of an expanded polyethylene with a hard, dense durometer as the foam element 50, backed by a 0.062 inch thick polypropylene shell as the panel 48. The shell is cut to form the loop 52.

Figure 7:
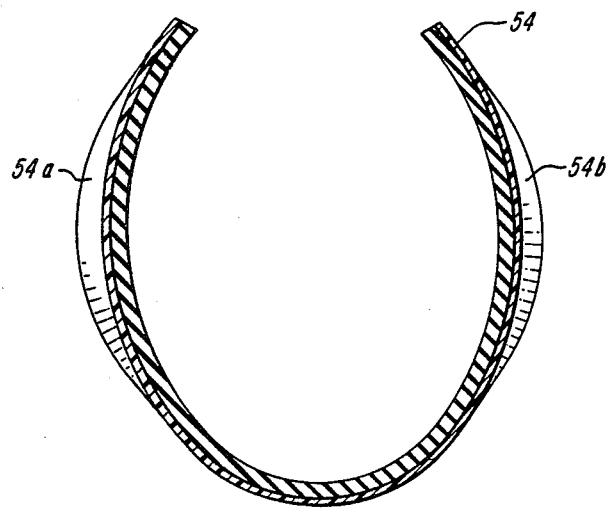

With reference to FIGS. 3, 6, and 7, the illustrated ankle wrap 42 has a stiffly compliant open cuff 54 that seats around the sides and back of a wearer's leg at the upper outward flare of the malleoli. The cuff 54 thus encircles the sides and back of a wearer's leg. An adjustable strap 56 which the cuff carries, spans across the front opening of the cuff, as FIG. 6 shows. The illustrated cuff 54 has a generally straight and normally horizontal upper rim and a saddle-shaped lower rim that forms relatively long side panels 54a and 54b, that seat over the malleoli, and a relatively short panel 54c that crosses the Achilles of the wearer.

The cuff of the wrap 42 further conforms anatomically to the substantially elliptical shape of a wearer's leg and hence has a generally elliptical horizontal cross-section with a longitudinal axis longer than the transverse axis, as appears in FIG. 7. Further, the cuff side panels 54a and 54b flare conically outward, to give the cuff a smaller circumference at the top and downward-facing outward conical flare, to conform anatomically to the outward flare of a human ankle at the upper portion of the malleoli.

The ankle wrap 42 can be fabricated in the foregoing manner with a cuff 54 of formed synthetic resin sheet or panel stock lined for added comfort with a layer of synthetic resin foam. The cuff is secured by integral loops, as illustrated, to a pliable tensile strap 56 fitted with rings and adjustable hook and loop or like fasteners. One preferred embodiment of the wrap 42 is made with an outer shell of 0.062 inch polypropylene with an inner liner of expanded polyethylene of medium density durometer.

With the foregoing structure, the ankle wrap 42 seats securely yet comfortably on a wearer and is anatomically keyed to the contour of the wearer to resist both rotation or twisting around the wearer and vertical movement along the wearer. The ankle wrap 42 thereby provides a substantially fixed upper anchorage for whatever stirrup straps are employed in the support device and particularly for carrying and deploying the bracing pad.

Figure 8:
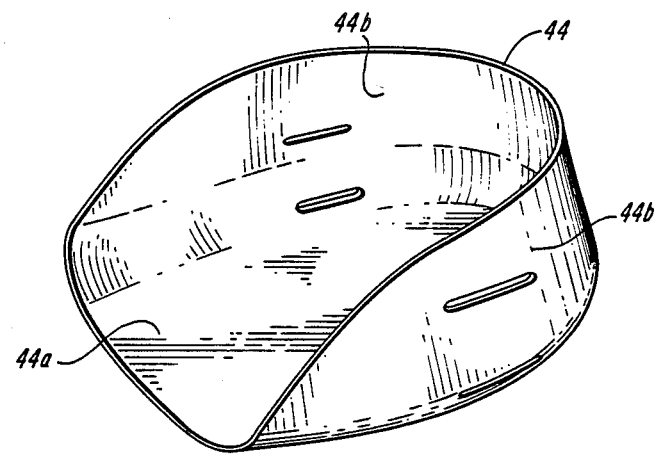
FIG. 8 further illustrates the heel cup of the support device of FIG. 3.

The illustrated heel cup 44, shown in FIGS. 3 and 8 receives and anatomically seats on the heel of the wearer, to move with the heel. Thus, during foot and ankle motion, particularly during lateral and medial inversion, the wearer's heel experiences minimal sliding within the heel cup. Instead, the heel cup moves with the heel of the wearer. The illustrated heel cup structure includes a sole panel 44a that extends under the sole of the wearer, forward from the heel to the back of the instep, and a side wall 44b that wraps around the soft bulbous sides of a wearer's heel. The heel cup 44 can, by way of example, be formed of a thin sheet of synthetic polymer.

The lateral strap 40, FIG. 3, is secured to the strap 56 of the ankle wrap 42, threads through the loop 52 on the bracing pad 36 and is secured at its lower end to the lateral sidewall of the heel cup 44. The strap 40 is adjustable in length and carries fastening elements, typically of the hook and loop type, to resist tensile elongation. The medial strap 46, when provided, is similarly secured at opposite ends to the ankle wrap 42 and to the medial sidewall of the heel cup 44, and is arranged to be adjustable and to resist tensile elongation. Both straps 40 and 46 preferably are otherwise pliable and compliant for user comfort.

The operation and functioning of the support device 34 as thus arranged and constructed is similar to that described above with reference to the support devices 10 and 22 of FIGS. 1 and 2, respectively.

Figure 9:
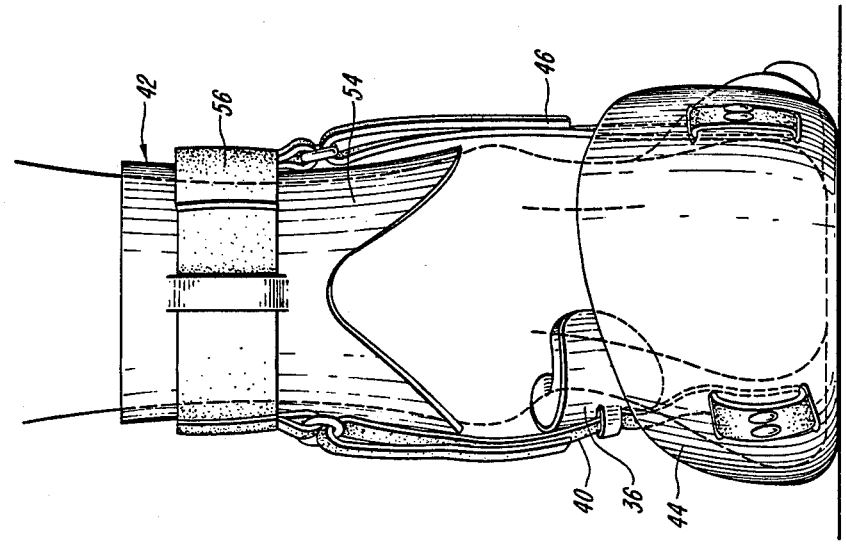
Figure 11:
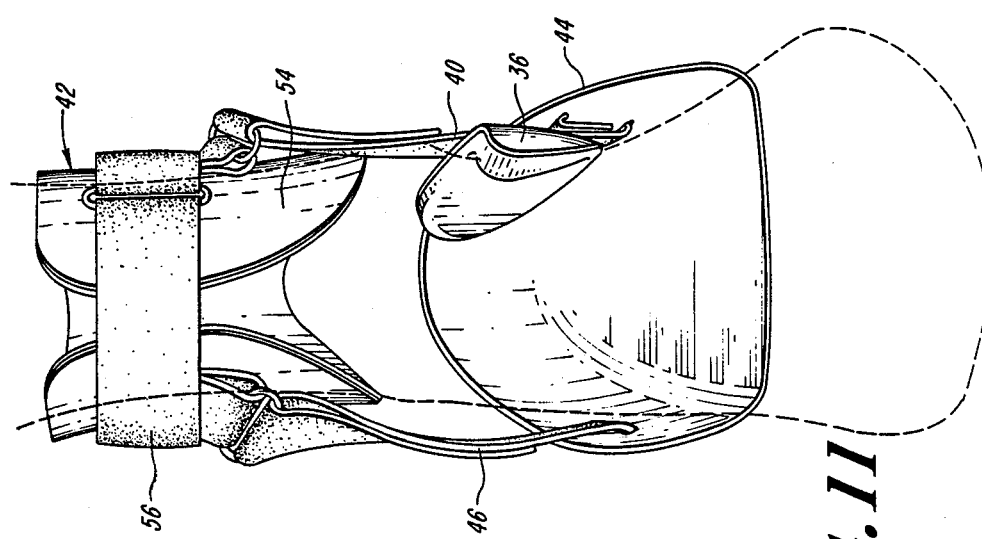

More particularly, FIGS. 9 and 11 show respectively back and front views of the support device 34 on a wearer during normal upright, e.g. standing, posture. The ankle wrap 42 encircles the ankle of the wearer with a secure and comfortable fit and is seated on the upper surfaces of the malleoli. The two stirrup straps 40 and 46 have minimal slack. The bracing pad 36 is disposed softly against the ankle bone and the underside of the lateral malleolus.

Figure 10:
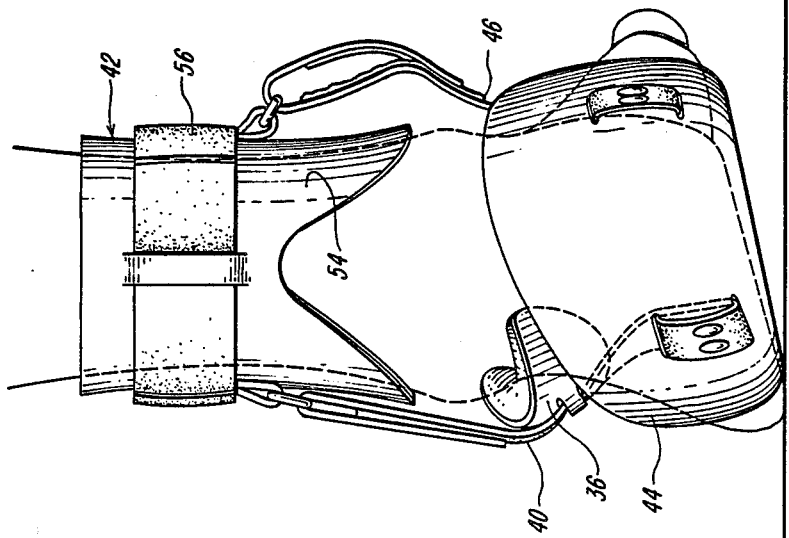
FIGS. 9 and 10 are showings, from the back, of the support device of FIG. 3 under conditions of normal posture and lateral inversion, respectively.
Figure 12:
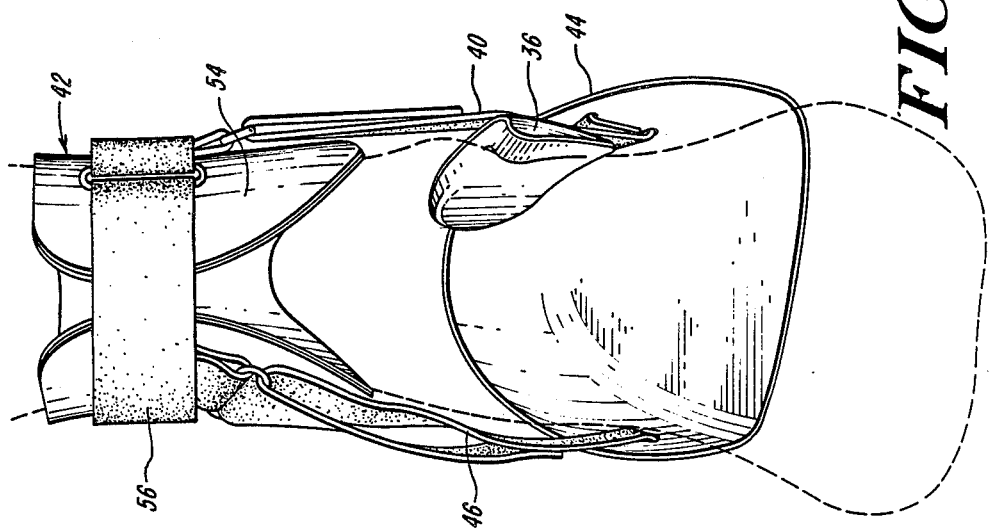
FIGS. 11 and 12 are front views corresponding to the rear views of FIGS. 9 and 10 and showing respectively normal posture and lateral inversion.

Upon lateral inversion of the wearer's ankle, as appears in FIGS. 10 and 12, the heel cup 44 rolls with the heel of the wearer, and the ankle wrap remains securely in position on the wearer. The resultant increased tension of the lateral strap 40 resists the inversion motion due to the tensile strength of the strap. Moreover, the increased tension of the strap combined with the lateral inversion of the ankle joint against it increasingly bears the bracing pad 36 inwardly and upwardly against the wearer, to additionally brace the ankle joint against further inversion motion.

Figure 13:
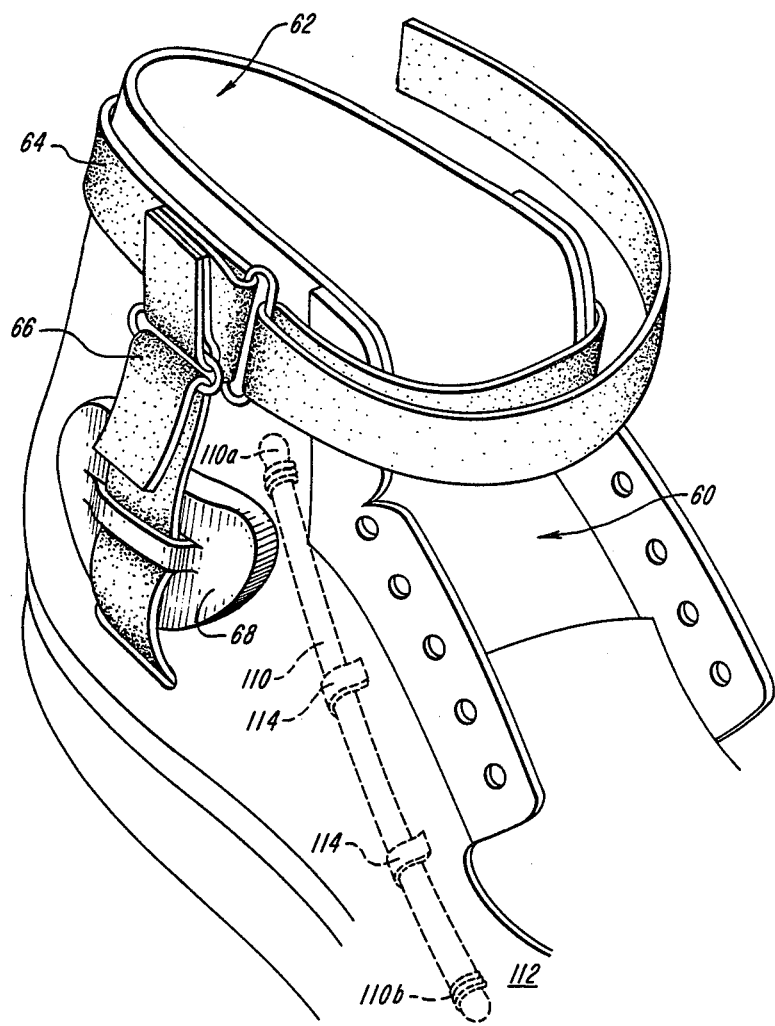
FIGS. 13 and 14 shows articles of footwear incorporating ankle support structures in accordance with the invention.

Alternative to the support devices of FIGS. 1–12 that are separate from footwear, ankle support bracing in accordance with the invention can be incorporated into footwear. In particular, FIG. 13 shows a shoe 60 of generally conventional construction with an ankle-height cuff 62 and fitted with ankle supporting brace elements in accordance with the invention. The illustrated shoe 60 has an upper that extends, as in a high sneaker and common work shoe, to above the ankle joint. The shoe carries an ankle strap 64 that wraps around the wearer's leg at the upper slopes of the malleoli and can be secured upon adjustment. An adjustable lateral stirrup-like strap 66 is secured to the lateral side of the shoe by an upper end connection to the ankle strap 62 and by a lower end connection to the shoe structure. A lateral bracing pad 68 is carried on the lateral strap to bear against the os calcis and the lateral malleoli of the wearer. In the illustrated shoe 60, the bracing pad is disposed outside the wall of the shoe. The invention can similarly be practiced with a bracing pad supposed within the wall of a shoe to bear directly against the wearer.

Figure 14:
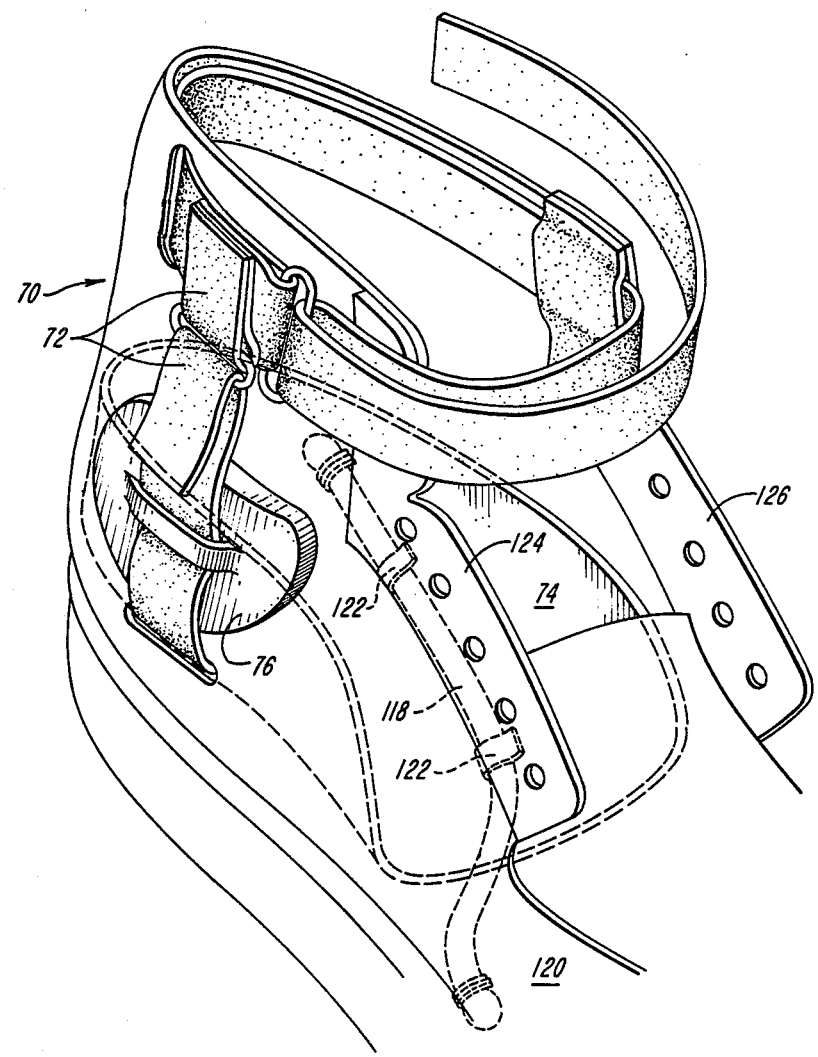

FIG. 14 shows another shoe 70 according to the invention with an ankle strap 72 incorporated at the upper rim of the shoe cuff. The shoe 70 includes a heel cup 74, shown partly with solid lines and partly with broken lines, that provides secure seating for the heel of the wearer and to which the lateral strap 72 preferably is secured at its lower end. This structure of the shoe 70 provides secure support and deployment for a bracing element 76.

Ankle support structures, including footwear, as described and as illustrated in FIGS. 1 through 14, can include an optional elastic strap element tensioned from the ankle cuff to urge dorsiflexion of the foot, i.e., lifting of the ball of the foot and the toes. This movement, which is opposite to the movement commonly termed pointing one's toes, is involved in generally all foot motion and movement. The provision of a dorsiflexion strap in accordance with the invention, as detailed below, is deemed advantageous with certain muscle weaknesses and in activities involving strenuous foot movement, as encountered for example by athletes.

Figure 15:
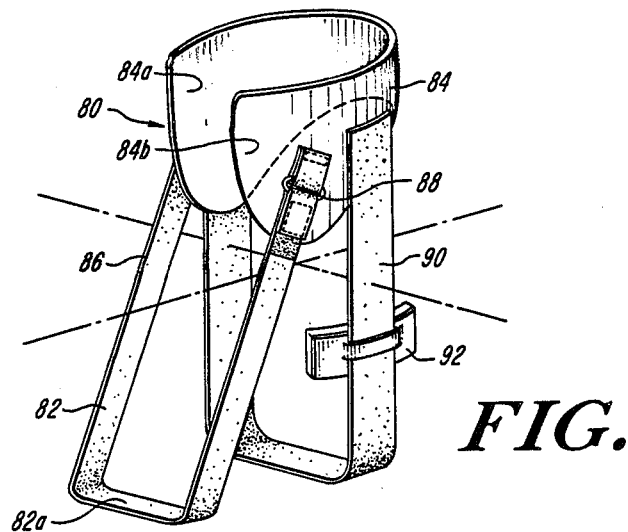
FIGS. 15 and 16 show embodiments that include dorsiflexion-assisting elements according to the invention.

FIG. 15 shows ankle support apparatus 80 similar to that described with reference to FIG. 1 and further having a dorsiflexion strap in the form of a stirrup-like strap element 82 arranged to span from the sides of an ankle cuff 84 to underneath the arch of the wearer's foot. The illustrated dorsiflexion element employs an elastic strap 86 and includes a length-adjusting buckle 88. The two ends are secured to opposite sides 84a and 84b of the ankle cuff. The illustrated strap element 82 is affixed to the ankle cuff 84 to extend diagonally, i.e. at an angle from the vertical, to position the base 82a of the stirrup configuration under the arch of the wearer. The support apparatus 80 further has a lateral stirrup element 90 and a bracing pad 92 similar to the corresponding elements of the brace 10 of FIG. 1.

The stirrup-like dorsiflexion strap element 82 can be formed entirely of elastic, aside from the buckle 88. One alternative is to employ a combination of one or more elastic elements, typically one in each arm of the stirrup configuration, and inelastic elements, such as an inelastic arch section, under the sole of the wearer's foot.

Figure 16:
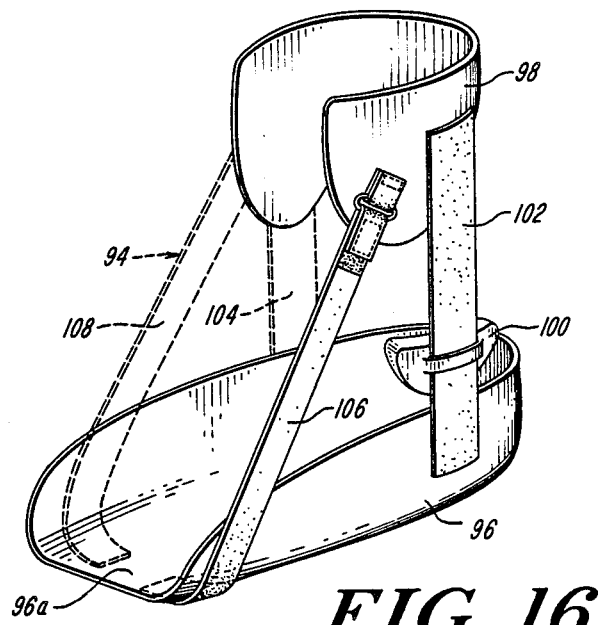

An ankle support device 116 with a dorsiflexion element according to the invention and having a heel cup 96, as appears in FIG. 16, has an ankle cuff 98 and a lateral bracing pad 100 and a lateral stirrup strap 102, all similar to corresponding elements of the ankle support device of FIG. 2. The FIG. 16 embodiment may also have a medial stirrup strap 104, as indicated with broken lines.

The illustrated dorsiflexion element of the device 94 includes a frontal extension 96a of the heel cup, which extends anteriorally under the arch of the wearer, and has at least one dorsiflexion strap 106 connected between the lateral side of the ankle cuff 98 and the lateral side of the forward extension 96a of the heel cup. For balance and symmetry in operation, a preferred construction employs a medial dorsiflexion strap 108 similarly connected on the medial side of the support device 94, as shown with broken lines. The dorsiflexion strap 106, which extends diagonally between the ankle cuff and the heel cup and includes a length and tensioning adjustment buckle as illustrated, has sufficient elasticity to remain under tension throughout a full excursion of movement of the ball of the foot. Note that the dorsiflexion strap elements 82 in the embodiment FIG. 15, and 106 and 108 in the embodiment FIG. 16, can be structured to be readily removable and yet replaceable so that the user can enjoy the ankle support devices 80 and 94, respectively, with or without the dorsiflexion elements.

Dorsiflexion assisting structures as provided by the invention can also be employed in footwear, such as the shoes 60 and 70 of FIGS. 13 and 14, respectively. The shoe 60 has an optional dorsiflexion element, shown with broken lines, that employs an elastic cord 110 spanning adjacent one set of lace eylets, and tensioned between the ankle cuff 62 of the shoe and a frontal surface 112 of the shoe vamp, as shown. The illustrated cord 110 is secured by heavy stitching at its ends 110a and 110b. Eyelets 114 affixed to the shoe typically are employed to guide and support the dorsiflexion cord 110. A dorsiflexion cord 110 as illustrated in FIG. 13 can be provided on either one or both sides of a shoe, i.e. a shoe can be provided with either or both a lateral and a medial dorsiflexion element.

FIG. 14 similarly shows a dorsiflexion assisting elastic cord 118 incorporated in the structure of the shoe 70. The cord 118, the ends of which are secured respectively to the shoe at the ankle cuff and on a forward location 120 on the shoe vamp, is illustrated as positioned by eyelets 122, along an eyelet flap 124. As in the shoe 60 of FIG. 13, the shoe 70 of FIG. 14 can employ either a single such dorsiflexion assisting cord 118 and alternatively can employ two such cords, one on either eyelet flap 124 and 126, or similarly arranged on either side of the lace opening or other frontal structure of the shoe.

Dorsiflexion assisting structures as described with reference to FIGS. 13–16, in one illustrative instance, extend from close to the base of the fifth metatarsal and run superiorly and obliquely to a further point of attachment on the side of the ankle cuff. In footwear, the dorsiflexion structure can be incorporated within the structure and not be visible, and alternatively can be outwardly apparent to enhance the distinctive appearance of the footwear. In each instance, it is understood that a dorsiflexion assisting strap assists in preventing inversion of the ankle, and enhances a competitor's walking, running and other foot movements, particularly when tired or to overcome weak or injured conditions. A medially arranged dorsiflexion assisting strap is understood to assist the anterior tibial muscle, whereas a strap arranged on the lateral side is understood to be of value under conditions of weak ankles, recurrent tendency to sprain, and recovery from a sprain.

It will thus be seen that the objects set forth above, among those made apparent from the preceding description, are efficiently attained with an ankle support and with shoe structures as shown and described. It is to be understood that all matter contained in the above description and shown in the drawings is within the scope of the claims appended hereto.

Having described the invention, what is claimed as new and secured by Letters Patent is:

1. Ankle support apparatus, for a human, comprising
   A. ankle wrap means for removably and replaceably fitting around the leg of a wearer closely above the ankle joint for seating upon the malleolus and substantially fixed in position relative to the wearer,
   B. heel-engaging means for removably and replaceably seating under the heel of a wearer,
   C. lateral strap means secured to and extending between said wrap means and said heel-engaging means at the lateral side relative to the wearer, said strap means being substantially inelastic longitudinally, thereby to resist tensile elongation, and
   D. lateral bracing pad means carried on said strap means for disposition, during normal standing ankle posture of the wearer and by said lateral strap means that is substantially free of slack, in engagement with the heel bone of the wearer and with the lateral malleolus of the wearer.
   E. said strap means being increasingly tensioned, upon lateral inversion of the ankle of the wearer, for resisting, with the tensile strength thereof, such inversion and for increasingly bearing said bracing pad means laterally against the heel bone and upward against the lateral malleolus, for further resisting such inversion.

2. Ankle support apparatus according to claim 1 having stirrup strap means having lateral and medial upper ends attached respectively to lateral and medial sides of said ankle wrap means and forming, at least in part, said heel-engaging means and said lateral strap means.

3. Ankle support apparatus according to claim 1 in which said bracing pad means includes means for engaging said lateral strap means for adjustable positioning of said pad means therealong and for resisting positional dislodgement upon tensioning of said lateral strap means.

4. Ankle support apparatus according to claim 1 in which said lateral bracing pad means has an inner bearing surface having a broad spade-like peripheral contour, and with a convex normally vertical transverse cross section.

5. Ankle support apparatus according to claim 1 in which said lateral bracing pad means is formed with a stiffly resilient outer panel and minimally compliant cushioning means on the inner surface thereof for said engagement with a wearer.

6. Ankle support apparatus according to claim 1
   A. in which said heel-engaging means includes heel cup means having a lower panel for seating under the wearer spanning from at least the arch of the wearer to the posterior of the heel and having side portion means for seatingly engaging the sides of the heel portion of the wearer,
   B. further comprising dorsiflexion-assisting elastic strap means elongated between first and second ends, a first of which is secured to said ankle cuff means and a second of which is secured to said heel cup means at an anterior location thereon.

7. Ankle support apparatus according to claim 1 further comprising medial strap means secured to and extending between said wrap means and said heel-engaging means at the medial side relative to the wearer, said medial strap means having limited slack during normal standing ankle posture of the wearer and being substantially inelastic longitudinally, thereby to resist tensile elongation.

8. Ankle support apparatus according to claim 7 in which said medial strap means includes longitudinal adjustment means.

9. Ankle support apparatus according to claim 1 in which said heel-engaging means includes heel cup means having a lower panel for seating under the wearer spanning at least from the posterior of the arch of the wearer to the posterior of the heel, and having side portion means for seatingly engaging the sides of the heel portion of the wearer along said span of said lower panel.

10. Ankle support apparatus according to claim 9 in which said heel cup means includes stiffly resilient sheet material having a heel-seating anatomical shape with said lower panel and side portion.

11. Ankle support apparatus according to claim 1 in which said lateral bracing pad means has an upper peripheral contour with a malleolus-receiving concavity for nestingly engaging the underside of the lateral malleolus of the wearer.

12. Ankle support apparatus according to claim 11 in which said lateral bracing pad means further has a convexly rounded lower peripheral contour.

13. Ankle support apparatus according to claim 1 in which said lateral bracing pad means has an inner bearing surface with a convex contour, as viewed in a normally vertical transverse plane, with maximal lateral projection for engagement below the lateral malleolus of the wearer and with an outwardly wedging diminished projection therebelow.

14. Ankle support apparatus according to claim 13 in which said inner bearing surface is contoured with an anatomical convexity, in a normally vertical transverse cross section, having a first shallow taper to said upper peripheral contour and with a second greater taper to said lower contour.

15. Ankle support apparatus according to claim 1 in which said ankle wrap means includes ankle cuff means having an anatomically contoured conical flare for seating on the outwardly flaring anatomy of the ankle joint at the upper portion of the malleoli, and substantially fixing said wrap means, by said seating engagement, vertically and rotationally relative to the wearer.

16. Ankle support apparatus according to claim 15 in which said ankle cuff means includes stiffly resilient sheet material having said flared anatomical contour.

17. Ankle support apparatus according to claim 15 in which said ankle cuff means further has an anatomically contoured generally elliptical cross section, in a normally horizontal plane.

18. Ankle support apparatus according to claim 15 in which said ankle wrap means further includes adjustable strap means connected with said cuff means for encircling the leg of the wearer and for adjustably fixing the circumference of said ankle wrap means.

19. Ankle support apparatus according to claim 1 further comprising dorsiflexion-assisting longitudinally elastic strap means secured for disposition under elastic tension between the leg of the wearer and an anterior portion of the foot of the wearer for imparting lift to the frontal toe portion of the foot of the wearer.

20. Ankle support apparatus according to claim 19 in which said dorsiflexion-assisting strap means includes a stirrup-like strap element elongated between two ends, each of which is secured to said ankle wrap means at the sides thereof, and disposed for passing under the instep of the wearer.

21. Ankle support apparatus according to claim 19 in which said dorsiflexion-assisting strap means includes a lateral strap element elongated between two ends, a first of which is secured to said ankle wrap means and a second of which is secured to said heel-engaging means at an anterior location thereon.

22. An ankle support according to claim 19 in which said dorsiflexion-assisting strap means includes tension adjustment means.

23. An article of footwear having a sole element and an upper element and including heel-engaging means for removably and replaceably seating under the heel of the wearer and further having an improvement for enhanced ankle support, said improvement comprising
   A. ankle wrap means for fitting around the leg of the wearer closely above the ankle joint for seating upon the malleolus and substantially fixed in position relative to the wearer,
   B. lateral strap means secured to and extending between said ankle wrap means and said heel-engaging means, at the lateral side relative to the wearer, said strap means being substantially inelastic longitudinally, thereby to resist tensil elongation, and
   C. lateral bracing pad means carried on said strap means for disposition, during normal standing ankle posture of the wearer and by said lateral strap means that is substantially free of slack, in engagement with the heel bone of the wearer and with the lateral malleolus of the wearer,
   D. said strap means being increasingly tensioned, upon lateral inversion of the ankle of the wearer, for resisting, with the tensil strength thereof, such inversion and for increasingly bearing said bracing pad means laterally against the heel bone and upward against the lateral malleolus for further resisting such inversion.

24. An article of footwear according to claim 23 further comprising a dorsiflexion-assisting longitudinally elastic strap means secured for disposition under elastic tension between said ankle wrap means and an anterior location for imparting lift to the toes of a wearer.

25. Ankle support apparatus, for a human, comprising
   A. ankle wrap means for removably and replaceably fitting around the leg of a wearer above the ankle joint and including stiffly resilient ankle cuff means having an anatomically contoured conical flare for seating on the outwardly flaring anatomy of the ankle joint at the upper portion of the malleoli and substantially fixing the position of said wrap means, by said seating engagement, relative to the wearer,
   B. heel-engaging means for removably and replaceably seating under the heel of a wearer,
   C. lateral strap means secured to and extending between said wrap means and said heel-engaging means at the lateral side relative to the wearer, said strap means being substantially longitudinally inelastic thereby to resist tensile elongation, and
   D. lateral bracing pad means carried on said strap means for disposition, by said strap means that has minimal slack during normal ankle posture, supportingly engaging the wearer at the heel bone and at the underside of the lateral malleolus.

* * * * *